United States Patent [19]

Kilbourn et al.

[11] 4,139,614

[45] Feb. 13, 1979

[54] ANTHELMINTIC PHOSPHONAMIDATE AND PHOSPHORAMIDATE COMPOSITIONS AND METHODS OF USE

[75] Inventors: Edward E. Kilbourn, Chalfont; Ernest Weiler, Ambler; William D. Weir, Levittown, all of Pa.

[73] Assignee: Rohm and Haas Company, Philadelphia, Pa.

[21] Appl. No.: 662,744

[22] Filed: Mar. 1, 1976

[51] Int. Cl.$^2$ .................. A61K 31/66; C07F 9/38
[52] U.S. Cl. ........................ 424/211; 260/938; 424/200
[58] Field of Search .................. 424/211; 260/938

[56] References Cited

FOREIGN PATENT DOCUMENTS 1139494 11/1962 Fed. Rep. of Germany ........... 260/438

OTHER PUBLICATIONS

Derwent Japanese Patent Reports, vol. 6, No. 10 (1967).

Primary Examiner—Leonard Schenkman

[57] ABSTRACT

This invention relates to novel anthelmintic compositions containing as the essential active ingredient, a compound of the formula:

$$R^1-N(R^2)-\overset{S}{\overset{\|}{C}}-N(R^3)-\overset{X}{\overset{\|}{P}}(R^4)(R^5)$$

wherein
$R^1$ is cylcoalkyl, or optionally substituted aralkyl, aryl, pyridyl, or pyrazinyl;
$R^2$ is hydrogen, alkyl, cycloalkyl, alkoxyalkyl, alkylthioalkyl, cyanoalkyl, alkenyl, or optionally substituted aralkyl or aryl;
$R^1$ and $R^2$ taken together with the nitrogen atom to which they are attached form an optionally substituted morpholino or piperidino group;
$R^3$ is hydrogen, alkyl, cycloalkyl, alkenyl, or optionally substituted aralkyl or aryl;
$R^4$ is alkoxy, haloalkoxy, dialkylamino, alkylthio, phenoxy or phenylthio; and
$R^5$ is alkyl, alkoxy, haloalkoxy, dialkylamino, alkylthio, phenyl, phenoxy or phenylthio; and
X is oxygen or sulfur;

and pharmaceutically acceptable metal salts and metal salt complexes thereof, and to methods of employing them in the treatment of intestinal parasites in animals, e.g. mammals, fish, and birds.

16 Claims, No Drawings

ANTHELMINTIC PHOSPHONAMIDATE AND PHOSPHORAMIDATE COMPOSITIONS AND METHODS OF USE

This invention relates to novel anthelmintic compositions and to methods of employing them in the treatment of intestinal parasites in animals, such as mammals, fish, and birds. The compositions of the present invention contain as the essential active ingredient at least one compound represented by the following formula:

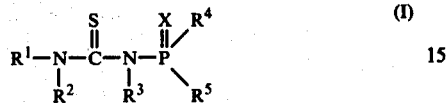

wherein
$R^1$ is
- (a) a $(C_3-C_8)$ cycloalkyl group, preferably a $(C_5-C_7)$ cycloalkyl group;
- (b) an optionally substituted aralkyl group of up to 11 carbon atoms, preferably an optionally substituted benzyl or phenethyl group;
- (c) an optionally substituted $(C_6-C_{14})$ aryl group;
- (d) an optionally substituted 2-pyridyl group; or
- (e) an optionally substituted pyrazinyl group;

$R^2$ is
- (a) a hydrogen atom;
- (b) a $(C_1-C_{10})$ alkyl group, preferably a $(C_1-C_6)$ alkyl group;
- (c) a $(C_3-C_8)$ cycloalkyl group, preferably a $(C_5-C_7)$ cycloalkyl group;
- (d) a $(C_2-C_{10})$ alkoxyalkyl group, preferably a $(C_2-C_6)$ alkoxyalkyl group;
- (e) a $(C_2-C_{10})$ alkylthioalkyl group, preferably a $(C_2-C_6)$ alkylthioalkyl group;
- (f) a $(C_1-C_6)$ cyanoalkyl group;
- (g) a $(C_3-C_6)$ alkenyl group, preferably a $(C_3-C_4)$ alkenyl group;
- (h) an optionally substituted aralkyl group of up to 11 carbon atoms, preferably an unsubstituted benzyl or unsubstituted phenethyl group, or
- (i) an optionally substituted $(C_6-C_{10})$ aryl group, preferably an unsubstituted phenyl group;

$R^1$ and $R^2$ taken together with the nitrogen atom to which they are attached form a morpholino or piperidino group, optionally substituted with up to two $(C_1-C_4)$ alkyl, preferably methyl, groups;

$R^3$ is
- (a) a hydrogen atom;
- (b) a $(C_1-C_{10})$ alkyl group, preferably a $(C_1-C_6)$ alkyl group;
- (c) a $(C_3-C_8)$ cycloalkyl group, preferably a $(C_5-C_7)$ cycloalkyl group;
- (d) a $(C_3-C_6)$ alkenyl group, preferably a $(C_3-C_4)$ alkenyl group;
- (e) an optionally substituted aralkyl group of up to 11 carbon atoms, preferably an unsubstituted benzyl or unsubstituted phenethyl group; or
- (f) an optionally substituted $(C_6-C_{10})$ aryl group, preferably an unsubstituted phenyl group;

$R^4$ is
- (a) a $(C_1-C_6)$ alkoxy group, preferably a $(C_1-C_4)$ alkoxy group;
- (b) a $(C_1-C_6)$ haloalkoxy group, preferably a $(C_1-C_4)$ haloalkoxy group;
- (c) a di-$(C_1-C_6)$ alkylamino group, preferably a di-$(C_1-C_4)$ alkylamino group;
- (d) a $(C_1-C_6)$ alkylthio group, preferably a $(C_1-C_4)$ alkylthio group;
- (e) a phenoxy group; or
- (f) a phenylthio group;

$R^5$ is
- (a) a $(C_1-C_6)$ alkyl group, preferably a $(C_1-C_4)$ alkyl group;
- (b) a $(C_1-C_6)$ alkoxy group, preferably a $(C_1-C_4)$ alkoxy group;
- (c) a $(C_1-C_6)$ haloalkoxy group, preferably a $(C_1-C_4)$ haloalkoxy group;
- (d) a di-$(C_1-C_6)$ alkylamino group, preferably a di-$(C_1-C_4)$ alkylamino group;
- (e) $(C_1-C_6)$ alkylthio group, preferably a $(C_1-C_4)$ alkylthio group; '(f) a phenyl group;
- (g) a phenoxy group; or
- (h) a phenylthio group; and X is an oxygen or sulfur atom, preferably an oxygen atom, and the pharmaceutically acceptable metal salts and metal salt complexes thereof.

The metal salts of this invention are the alkali and alkaline earth metal salts of the compounds of Formula I wherein at least one of $R^2$ and $R^3$ is a hydrogen atom. The preferred metal salt is the sodium salt.

The metal salt complexes of this invention may be represented by the following formula, which is presented for illustrative purposes only:

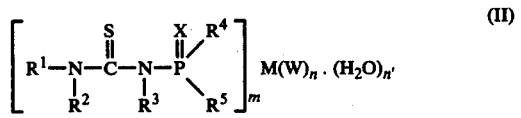

wherein
$R^1$, $R^2$, $R^3$, $R^4$, $R^5$ and X are as defined for Formula I;

M is a metal cation which can be selected from groups IIA, IIIA, IB, IIB, VIIB, and VIII of the periodic table;

W is an anion such as chloride, bromide, iodide, sulfate, bisulfate, phosphate, nitrate, perchlorate, carbonate, bicarbonate, hydroxide, acetate, oxalate malate, citrate, and the like;

m is an integer of 1–2;
n is an integer of 1–2; and
n' is an integer of 0–4.

Among the compounds depicted by Formula II above, the preferred compounds are those wherein the metal cation is a transition metal such as copper, zinc, nickel, cobalt, tin, cadmium, or manganese; or an alkaline earth metal such as calcium or magnesium, and wherein the anion is chloride, bromide, nitrate, or sulfate or hydroxide. The most preferred salts are those wherein the metal cation is copper, zinc, nickel, cobalt, tin, cadmium or manganese and the anion is hydroxide.

In Formulas I and II above, $R^2$ is preferably a hydrogen atom or a benzyl group, and $R^3$ is preferably a hydrogen atom.

The preferred compounds of this invention can be represented by the formula:

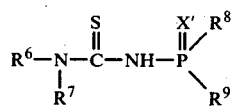

wherein
R⁶ is
(a) a ($C_5$-$C_7$) cycloalkyl group, preferably a cyclohexyl group;
(b) a benzyl or phenethyl group;
(c) a phenyl, benzyl, or phenethyl group, preferably a phenyl group, substituted with up to three, preferably up to two, ($C_1$-$C_4$) alkyl groups, preferably methyl groups, ($C_1$-$C_4$) alkoxy groups; preferably methoxy groups, di-($C_1$-$C_4$) alkylamino groups, preferably dimethylamino groups, ($C_1$-$C_4$) hydroxyalkyl group; halogen atoms, preferably chlorine atoms; haolmethyl groups, preferably trifluoromethyl groups; hydroxy groups; or cyano groups;
(d) a fluorenyl group;
(e) a 2-pyridyl group optionally substituted with up to two, but preferably one, ($C_1$-$C_4$) alkyl, preferably methyl, groups, or halogen, preferably chlorine, atoms; or
(f) a pyrazinyl group;
R⁷ is a hydrogen atom or a benzyl group;
R⁸ is
(a) a ($C_1$-$C_4$) alkoxy group, preferably an ethoxy group;
(b) a ($C_1$-$C_4$) haloalkoxy group, preferably a trichloroethoxy group;
(c) a di-($C_1$-$C_4$) alkylamino group, preferably a dimethylamino group; or
(d) a ($C_1$-$C_4$) alkylthio group, preferably a propylthio group;
R⁹ is
(a) a ($C_1$-$C_4$) alkyl group, preferably an ethyl group;
(b) a ($C_1$-$C_4$) alkoxy group, preferably an ethoxy group;
(c) a ($C_1$-$C_4$) haloalkoxy group, preferably a trichloroethoxy group;
(d) a di-($C_1$-$C_4$) alkylamino group, preferably a dimethylamino group; or
(e) a ($C_1$-$C_6$) alkylthio group, preferably a ($C_1$-$C_5$) alkylthio group; and
X' is an oxygen or sulfur atom, preferably an oxygen atom;
and the pharmaceutically acceptable metal salts and metal salt complexes thereof.

Among the preferred compounds, the more preferred are those wherein R⁸ is an ethoxy group, and R⁹ is an ethoxy group, an isobutylthio group, or a sec-butylthio group.

As used in the specification and claims, the term "substituted", when used to modify aralkyl, aryl, pyridyl, or pyrazinyl groups, indicates that such groups are substituted with one or more substituents selected from the group consisting of ($C_1$-$C_4$) alkyl, ($C_1$-$C_4$) alkoxy, ($C_1$-$C_4$) alkythio, ($C_1$-$C_4$) alkylsulfinyl, ($C_1$-$C_4$) alkylsulfonyl, di-($C_1$-$C_4$) alkylamino, ($C_1$-$C_4$) haloalkyl, ($C_1$-$C_4$) hydroxyalkyl, cyano, nitro, hydroxy, and halogen. In the pyridyl and pyrazinyl rings, up to two substituents are preferred, while in the aralkyl and aryl groups, up to three substituents are preferred, up to two substituents being more preferred.

As used in the specification and claims, the terms alkyl, alkenyl, alkoxy, alkoxyalkyl, alkylthio, alkylthioalkyl, alkylsulfinyl, alkylsulfonyl, dialkylamino, haloalkyl, haloalkoxy, hydroxyalkyl, cyanoalkyl, aralkyl, and the like, are meant to include branched as well as straight chain groups.

Representative R¹ substituents include, for example, cyclopropyl, cyclohexyl, cycloheptyl, phenyl, 3,5-dichlorophenyl, 4-chlorophenyl, 3,4-dichlorophenyl, 2,4-dichlorophenyl, 2,4,6-trichlorophenyl, 2,3,4,5,6-pentachlorophenyl, 4-bromophenyl, 2-chloro-4-bromophenyl, 4-fluorophenyl, 3,5-ditrifluoromethylphenyl, 2methylphenyl, 4-methylphenyl, 2,5-dimethylphenyl, 2-chloro-4-methylphenyl, 2,4-dichloro-3,5-dimethylphenyl, 2-ethyl-4-methoxyphenyl, 4-butylphenyl, 4-methylthiophenyl, 3-methylsulfinylphenyl, 4-methylsulfonylphenyl, 5-methoxyphenyl, 2-ethoxyphenyl, 4-dimethylaminophenyl, 4-nitrophenyl, 3-cyanophenyl, benzyl, 3,5-dimethylbenzyl, 3,5-dihydroxyphenyl, 4-hydroxybutylphenyl, 4-bromo-3,5-dichlorobenzyl, phenethyl, α-methylbenzyl, 4-methylphenethyl, 4-methoxyphenethyl, naphthyl, 4,6-dichloronaphthyl, anthryl, 5,6-dichloroanthryl, phenanthryl, 4-fluorenyl, 4-chloro-9-fluorenyl, 4,5-dimethyl-9-fluorenyl, 2-pyridyl, 2-(5-chloropyridyl), 2-(3,5-dimethylpyridyl), pyrazinyl, 2-(5-chloropyrazinyl), 2-(5-methylpyrazinyl), and the like.

Representative R² substituents include, for example, hydrogen, methyl, butyl, tert-butyl, nonyl, cyclobutyl, cyclohexyl, 2-ethoxyethyl, 4-butoxybutyl, 2-cyanoethyl, 4-cyanobutyl, 3-ethylthiopropyl, 2-butylthioethyl, allyl, phenyl, 3,5-dichlorophenyl, 2-methylphenyl, 4-cyanophenyl, 4-nitrophenyl, 4-methoxy-2-methylphenyl, benzyl, 3,5-ditrifluoromethylbenzyl, phenethyl, α-methylbenzyl, 3-phenylpropyl, 3,5-dichlorophenethyl, naphthyl, 4,6-dimethylnaphthyl, and the like.

Representative R³ substituents include, for example, hydrogen, methyl, butyl, isobutyl, hexyl, cyclopentyl, cyclohexyl, allyl, 2-butenyl, phenyl, 2-methylphenyl, 3,5-dichlorophenyl, benzyl, 4-methylbenzyl, phenethyl, naphthyl, 3-methylnaphthyl, and the like.

Representative R⁴ substituents include, for example, methoxy, ethoxy, sec-butoxy, pentoxy, trichloroethoxy, chloropropoxy, trifluoroethoxy, dimethylamino, dipropylamino, methylthio, propylthio, isobutylthio, hexylthio, phenoxy, phenylthio, and the like.

Representative R⁵ substituents include, for example, methyl, ethy, propyl, isopropyl, butyl, sec-butyl, pentyl, hexyl, ethoxy, propoxy, isopropoxy, butoxy, pentoxy, chlorobutoxy, trifluoroethoxy, bromopentoxy, dimethylamino, dihexylamino, ethylthio, propylthio, isobutylthio, sec-butylthio, pentylthio, phenyl, phenoxy, phenylthio, and the like.

Examples of the compounds embraced by this invention include:
N-(N'-butyl N'-cyclohexyl)aminothiocarbonyl O,O-diethyl phosphoramidate
O,O-diethyl piperidinothiocarbonyl phosphoramidate
N-(2-cyanophenyl)aminothiocarbonyl O,O-diethyl phosphoramidate
N-(N'-3,4-dichlorophenyl N'-ethoxymethyl)aminothiocarbonyl O,O-diethyl phosphoramidate
N-(N'-3,5-dichlorophenyl N'-2-ethylthioethyl)aminothiocarbonyl O,O-diethyl phosphoramidate N-allyl N-(3,5-dichlorophenyl)aminothiocarbonyl O,O-diethyl phosphoramidate N-[N'-(4-cyanoethyl) N'-(3,5-dichlorophenyl)]aminothiocarbonyl O,O-diethyl phosphoramidate N-benzyl N-(3,5-dichlorophenyl)aminothiocarbonyl O,O-diethyl phosphoramidate O,O-dibutyl N-(N'-2,4-dichlorophenyl N'-phenyl)aminothiocarbonyl phosphoramidate O,O-diethyl N-(2-naphthyl)aminothiocarbonyl phosphoramidate N-benzylaminothiocarbonyl O-ethyl O-propyl phosphoramidate N-(N',N'-dibenzyl)aminothiocarbonyl O,O-diethyl phosphoramidate O,O-dimethyl N-(3-phenylpropyl)aminothiocarbonyl phosphoramidate N-(3,5-dichlorophenyl)aminothiocarbonyl O,O-diphenyl phosphoramidate O-ethyl N-(4-hydroxybutyl)aminothiocarbonyl S-(1-methylpropyl) phosphoramidothioate N-(3,5-ditrifluoromethylphenyl)aminothiocarbonyl O-ethyl O-phenyl phosphoramidate O,O-diethyl N-(2-fluorenyl)aminothiocarbonyl phosphoramidate O,O-diethyl N-(3,5-dimethyl-2-pyridyl)aminothiocarbonyl phosphoramidate N-(4-chloro-2-pyridyl)aminothiocarbonyl O,O-diethyl phosphoramidate O,O-diethyl N-(5-ethyl-2-pyridyl)aminothiocarbonyl phosphoramidate N-cyclohexylaminothiocarbonyl O-ethyl S-(2-methylpropyl) phosphoramidothioate O-ethyl S-(2-methylpropyl) N-morpholinothiocarbonyl phosphoramidothioate N-benzylaminothiocarbonyl S,S-dipropyl phosphoramidodithioate N-(4-cyanobenzyl) aminothiocarbonyl O,S-diethyl phosphoramidothioate O-ethyl S-(2-methylpropyl) N-phenethylaminothiocarbonyl phosphoramidothioate N-(2,4-dichlorophenyl)aminothiocarbonyl S,S-bis-(1-methylpropyl) phosphoramidotrithioate N-(3,5-ditrifluoromethylphenyl)aminothiocarbonyl O-ethyl S-(2-methylpropyl) phosphoramidothioate S-butyl N-(4-methoxyphenyl)aminothiocarbonyl S-propyl phosphoramidodithioate N-dimethyl O-ethyl N-(4-methylthiophenyl)aminothiocarbonyl phosphorodiamidate N-(4-ethylsulfonylphenyl)aminothiocarbonyl O-ethyl S-methylethyl phosphoramidothioate N-(3-cyanophenyl)aminothiocarbonyl O-ethyl N-methyl S-methylethyl phosphoramidothioate N-[N'-(4-dimethylaminophenyl) N'-methyl]aminothiocarbonyl O-ethyl N-methyl S-pentyl phosphoramidothioate N-[N'-(3,5-dichlorophenyl) N'-(4-methylphenyl)]aminothiocarbonyl O-ethyl S-propyl phosphoramidothioate S-(1-methylpropyl) N-(4-nitrophenyl)aminothiocarbonyl O-phenyl phosphoramidothioate O-ethyl N-(3-methyl-4-methylthiophenyl)aminothiocarbonyl S-propyl phosphoramidothioate O-ethyl S-(2-methylpropyl) N-(2-pyridyl)aminothiocarbonyl phosphoramidothioate N-(2,4-dichlorophenyl)aminothiocarbonyl O,S-diethyl phosphoramidothioate N-(2,4-dichlorophenyl)aminothiocarbonyl O-ethyl S-methylethyl phosphoramidothioate S-butyl N-(3,5-dichlorophenyl)aminothiocarbonyl O-methyl phosphoramidothioate N-(3-bromo-5-chlorophenyl)aminothiocarbonyl O-ethyl S-(2-methylpropyl)phosphoramidothioate O-ethyl N-(4-fluorophenyl)aminothiocarbonyl N-(4-methoxyphenethyl) S-(1-methylpropyl) phosphoramidothioate N-(2,5-dichlorophenyl)aminothiocarbonyl O-ethyl S-(1-methylpropyl) phosphoramidothioate N-(3,5-dichlorophenyl)aminothiocarbonyl N'-dimethyl O-propyl phosphorodiamidate Ethyl O-ethyl N-(4-methylphenyl)aminothiocarbonyl phosphonamidate N-(4-chlorophenyl)aminothiocarbonyl S,S-dipropyl phosphoramidodithioate S,S-bis-(1-methylpropyl) N-phenethylaminothiocarbonyl phosphoramidothioate S-(1-methylpropyl) O-propyl N-(3,5-bis-trifluoromethylphenyl) aminothiocarbonyl phosphoramidothioate N-(2,4-dimethylphenyl)aminothiocarbonyl O-ethyl S-(1-methylpropyl) phosphoramidothioate O-ethyl N-(2-methoxyphenyl)aminothiocarbonyl S-pentyl phosphoramidothioate N-(4-diethylaminophenyl)aminothiocarbonyl O-ethl S-(1-methylpropyl) phosphoramidothioate S-(1-methylpropyl) O-propyl N-pyrazinylaminothiocarbonyl phosphoramidothioate N-(4-chlorophenyl)aminothiocarbonyl O-ethyl S-phenyl phosphoramidothioate O-ethyl N-(N'-4-fluorenyl)aminothiocarbonyl S-(2-methylpropyl) phosphoramidothioate N-{N'-[9-(3,6-dichlorofluorenyl)]aminothiocarbonyl} O-ethyl S-(1-methylpropyl) phosphoramidothioate N-(2-anthryl)aminothiocarbonyl O-ethyl S-n-propyl phosphoramidothioate N-[1-(3-methylanthryl)aminothiocarbonyl] O-ethyl S-(1-methylpropyl) phosphoramidothioate and the pharmaceutically acceptable metal salts and metal salt complexes thereof, and the like.

Compounds of this invention can be prepared by a variety of methods. One method involves contacting an appropriate aralkyl, aromatic or heterocyclic amine with an appropriately substituted phosphono- or phosphoro- isothiocyanate. This reaction can be represented by the following equation:

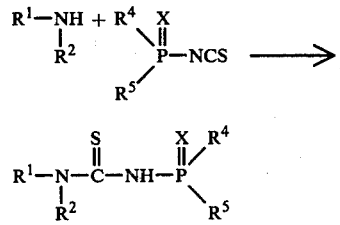

wherein $R^1$, $R^2$, $R^4$, $R^5$, and X are as defined for Formula I.

The reaction is generally carried out in the presence of an aprotic solvent such as glyme, acetone, acetonitrile, ethyl acetate, butyl acetate, diethyl ether, or mixtures thereof, at a temperature range of about 15° C. to about 120° C., preferably at about 25° C. to about 45° C. A substantially equimolar ratio of reactants is preferred, but an excess of the phosphoroisothiocyanate can be used. The desired product can be separated from the reaction mixture by conventional means, such as fractional crystallization, chromatography, extraction, or the like.

Another method for preparing compounds within the scope of this invention involves contacting an appropriate aralkyl, aromatic, or heterocyclic amine with an appropriately substituted chlorothiocarbonyl phosphonamidate or phosphoramidate. This reaction can be represented by the following equation:

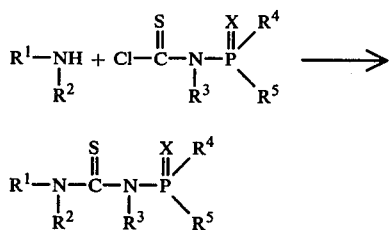

wherein $R^1$, $R^2$, $R^3$, $R^4$, $R^5$, and X are as defined for Formula I, with the exception that $R^3$ cannot be a hydrogen atom.

This reaction is generally carried out in the presence of an aprotic solvent such as glyme, acetone, acetonitrile, ethyl acetate, butyl acetate, diethyl ether, or mixtures thereof, at a temperature range of about 15° C. to about 120° C., preferably at about 25° C. to about 45° C. An acid acceptor such as a tertiary amine can be employed as a scavenger in this preparation. Representative acid acceptors include pyridine, trimethylamine, triethylamine, and the like. However, an excess of the amine reactant can also serve as the acid acceptor. Generally, a substantially equimolar ratio of reactants is preferred, but an excess of two or more moles of amine can be employed if the amine is intended to serve the dual function of reactant and acid acceptor. The desired product can be separated from the reaction mixture by conventional means.

A third method of preparing compounds of this invention involves contacting an appropriate phosphonamidate or phosphoramidate with an appropriate isothiocycyanate. This reaction can be represented by the following equation:

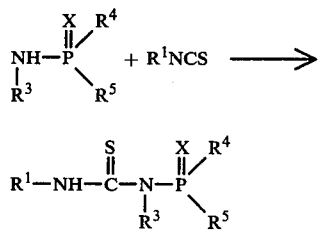

wherein $R^1$, $R^3$, $R^4$, $R^5$ and X are as defined for Formula I.

The reaction is generally carried out in the presence of an aprotic solvent such as glyme, acetone, acetonitrile, ethyl acetate, butyl acetate, diethyl ether, or mixtures thereof, at a temperature range of about 20° C. to about 60° C., room temperature being preferred. A substantially equimolar ratio of reactants is preferred. The desired product can be separated from the reaction mixture by conventional means.

The metal salts of this invention are prepared by (1) adding an alkali or alkaline earth metal hydroxide or hydride to a suspension of the appropriate phosphonamidate or phosphoramidate in a suitable solvent, (2) stirring the mixture until a solution forms, and (3) freeze drying the solution, or in the alternative, (4) concentrating the solution in vacuo at room temperature and drying the residue in a vacuum oven at room temperature.

The metal salt complexes are prepared by (1) reacting, in an aqueous or alcoholic medium, a phosphonamidate or phosphoramidate of this invention, with a metal salt selected from group IIA, IIIA, IB, IIB, VIIB, or VIII of the periodic table, (2) filtering off the precipitate which forms, and (3) washing and drying the precipitate to give the product.

All of the starting materials used in the preparation of the compounds of this invention are known compounds or are readily prepared by methods available to those skilled in the art.

By way of demonstration, the following examples are offered to illustrate this invention and are not to be construed as limitations thereof.

EXAMPLE 4

Preparation of O,O-diethyl N-(4-nitrophenyl)aminothiocarbonyl phosphoramidate

To a solution of 3.46 g. (0.025 mole) of 4-nitroaniline in 50 ml. of glyme is added 4.87 g. (0.025 mole) of O,O-diethyl phosphoroisothiocyanatoate. The solution is allowed to stand at room temperature for 18 hours after which it is heated to reflux for 3 hours. The product precipitates from the glyme solution to yield 1.5 g. (18%).

EXAMPLE 5

Preparation of O,O-diethyl N-(3,5-bis-trifluoromethylphenyl)aminothiocarbonyl phosphoramidate To a solution of 8.23 g. (0.0359 mole) of 3,5-bis-trifluoromethylaniline in 100 ml. of glyme is added 7 g. (0.0359 mole) of O,O-diethyl phosphoroisothiocyanatoate. The solution is allowed to stand at room temperature for 24 hours and is concentrated in vacuo. The precipitate is crystallized from hexane and recrystallized from methylcyclohexane. The product yield is 10 g. (67%).

EXAMPLE 6

Preparation of N-(3,5-dichlorophenyl)aminothiocarbonyl O,O-diethyl phosphoramidate To a solution of 5.98 g. (0.0359 mole) of 3,5-dichloroaniline in 100 ml. of glyme is added 7 g. (0.0359 mole) of O,O-diethylphosphorosiothiocyanatoate. The solution is allowed to stand at room temperature for 24 hours and is concentrated in vacuo. The precipitate is crystallized from methylcyclohexane to afford 8.5 g. (56%) of product.

EXAMPLE 7

Preparation of N-(3,5-dichlorophenyl)aminothiocarbonyl O-ethyl S-methyl phosphoramidothioate To a solution of 1.62 g. (0.01 mole) of 3,5-dichloroaniline in 5 ml. of glyme is added 1.97 g. (0.01 mole) of O-ethyl S-methyl phosphoroisothiocyanatothioate. The reaction solution is allowed to stand at room temperature for 18 hours. The product is obtained by pouring the reaction solution into an excess of water and isolating the precipitate by vacuum filtration. The product yield is 2.55 g. (71%).

EXAMPLE 8

Preparation of N-(3,5-dichlorophenyl)aminothiocarbonyl O,S-diethyl phosphoramidothioate To a solution of 1.92 g. (0.0018 mole) of 3,5-dichloroaniline in 7 ml. of glyme is added 2.5 g. (0.0118 mole) of O,S-diethyl phosphoroisothiocyanatothioate. The product is obtained by pouring the reaction solution into an excess of water, vacuum filtering the suspension which forms and recrystallizing the isolated precipitate from methylcyclohexane. The product yield is 1.2 g. (27.3%).

EXAMPLE 9

Preparation of N-(3,5-dichlorophenyl)aminothiocarbonyl O-ethyl S-propyl phosphoramidothioate To a solution of 1.62 g. (0.01 mole) of 3,5-dichloroaniline in 5 ml. of glyme is added 2.25 g. (0.01 mole) of O-ethyl S-propyl phosphoroisothiocyanatothioate. The product is obtained by pouring the reaction solution into an excess of water, vacuum filtering the suspension which forms, and recrystallizing the isolated precipitate from methylcyclohexane. The product yield is 1.8 g. (47.5%).

EXAMPLE 11

Preparation of N-(3,5-dichlorophenyl)aminothiocarbonyl O-ethyl S-methylethyl phosphoramidothioate To a solution of 2.88 g. (0.0178 mole) of 3,5-dichloroaniline in 5 ml. of glyme is added 0.4 g. (0.0178 mole) of O-ethyl S-methylethyl phosphoroisothiocyanatothioate. The solution is heated to reflux and allowed to stand at room temperature for 2 hours. The suspension which forms is vacuum filtered and the filter cake is washed with 10 ml. of glyme, 20 ml. of ether, and dried to afford 2 g. (29%) of product.

EXAMPLE 14

Preparation of N-(3,5-dichlorophenyl)aminothiocarbonyl O-ethyl S-(2-methylpropyl) phosphoramidothioate To a solution of 1.62 g. (0.01 mole) of 3,5-dichloroaniline in 5 ml. of glyme is added 2.39 g. (0.01 mole) of O-ethyl S-(2-methylpropyl) phosphoroisothiocyanatothioate. The solution is heated to reflux and allowed to stand at room temperature for 3 days. The solution is poured into an excess of water and the semi-solid precipitate which forms is isolated. The product is slurried in 50 ml. of hexane and vacuum filtered. The filter cake is dried to afford 1.8 g. (45%) of product.

EXAMPLE 15

Preparation of N-(3,5-dichlorophenyl)aminothiocarbonyl O-ethyl S-(1-methylpropyl) phosphoramidothioate To a solution of 3.24 g. (0.02 mole) of 3,5-dichloroaniline in 15 ml. of glyme is added 4.8 g. (0.02 mole) O-ethyl S-(1-methylpropyl) phosphoroisothiocyanatothioate. The solution is allowed to stand at room temperature for 18 hours and then poured into an excess of water. The semi-solid precipitate which forms is isolated and slurried in 50 ml. of hexane. The hexane slurry is filtered to afford 3.25 g. (40.5%) of product, m.p. 123°–125° C. The product is recrystallized from methylcyclohexane to afford 2.5 g. (31%) of product.

EXAMPLE 19

Preparation of O-ethyl N-(4-methylphenyl)aminothiocarbonyl S-(1-methylpropyl) phosphoramidothioate To a solution of 1.07 g. (0.01 mole) of 4-methylaniline in 5 ml. of glyme is added 2.39 g. (0.01 mole) of O-ethyl S-(1-methylpropyl) phosphoroisothiocyanatothioate (exothermic reaction). The solution is allowed to stand at room temperature for 6 days and is poured into an excess of water (300 ml.). The suspension which forms is vacuum filtered and the filter cake is slurried in 50 ml. of hexane, filtered, and dried to afford 1.6 g. (47%) of product.

EXAMPLE 20

Preparation of O-ethyl N-(4-methoxyphenyl)aminothiocarbonyl S-(1-methylpropyl) phosphoramidothioate To a solution of 1.23 g. (0.01 mole) of 4-methoxyaniline in 5 ml. of glyme is added 2.39 g. (0.01 mole) of O-ethyl S-(1-methylpropyl) phosphoroisothiocyanatothioate (exothermic reaction). The solution is allowed to stand at room temperature for 18 hours and is poured into an excess of water. The suspension which forms is vacuum filtered and the filter cake is slurried in 100 ml. of hexane, filtered, and dried to afford 2.4 g. (66.5%) of product.

EXAMPLE 21

Preparation of N-(4-dimethylaminophenyl)aminothiocarbonyl O-ethyl S-(1-methylpropyl) phosphoramidothioate To a solution of 1.36 g. (0.01 mole) of N,N-dimethyl-4-phenylenediamine in 5 ml. of glyme is added 2.3 g. (0.01 mole) of O-ethyl S-(1-methylpropyl) phosphoroisothiocyanatothioate (exothermic reaction). The solution is allowed to stand at room temperature for 24 hours and is poured into an excess of water. The black tarry precipitate is slurried in hexane and then vacuum filtered. The filter cake is re-slurried in 15 ml. of ethyl acetate, vacuum filtered and dried to afford 0.9 g. (24.6%) of product.

EXAMPLE 24

Preparation of N-(3,5-dichlorophenyl)aminothiocarbonyl O,O-bis-(2-trichloroethyl) phosphoramidate To a solution of 32.4 g. (0.02 mole) of 3,5-dichloroaniline in 10 ml. of glyme is added 8 g. (0.02 mole) of O,O-bis-(2-trichloroethyl) phosphoroisothiocyanatoate. The product is obtained by pouring the reaction solution into an excess of water, vacuum filtering the suspension which forms, and recrystallizing the isolated precipitate from isopropanol. The product yield is 0.5 g. (4.5%).

EXAMPLE 25

Preparation of N-(3,5-dichlorophenyl)aminothiocarbonyl N',N''-(bis-dimethyl) phosphorotriamidate To a solution of 3.24 g. (0.02 mole) of 3,5-dichloroaniline in 10 ml. of glyme, is added 3.86 g. (0.02 mole) of N,N-bis-dimethyl phosphoroisothiocyanate. The desired product precipitates from the glyme solution and is isolated by vacuum filtration to yield 3.2 g. (45.6%) of product.

EXAMPLE 26

Preparation of N-(3,5-dichlorophenyl)aminothiocarbonyl N'-dimethyl O-ethyl phosphorodiamidate To 1.62 g. (0.01 mole) of 3,5-dichloroaniline in 10 ml. of glyme is added 1.94 g. (0.01 mole) of N-dimethyl O-ethyl phosphoroisothiocyanate. The glyme solution is allowed to stand at room temperature for 4 days, after which time the product precipitates from solution and is isolated by vacuum filtration to yield 1.5 g. (43%) of product

EXAMPLE 35

Preparation of O,O-diethyl N-(2-pyridyl) aminothiocarbonyl phosphoramidate

To a 1.88 g. (0.02 mole) solution of 2-aminopyridine in 8 ml. of glyme is added 3.9 g. (0.02 mole) of O,O-diethyl phosphoroisothiocyanatoate. The reaction solution is allowed to stand at room temperature for one hour. The product is obtained by pouring the reaction solution into an excess of water and isolating the precipitate by vacuum filtration. The product yield is 2.9 g. (50%).

EXAMPLE 36

Preparation of O,O-diethyl N-[2-(5-methylpyridyl)]aminothiocarbonyl phosphoramidate To a solution of 2.16 g. (0.02 mole) of 2-amino-5-methylpyridine in 8 ml. of glyme is added 3.9 g. (0.02 mole) of O,O-diethyl phosphoroisothiocyanatoate. The reaction solution is allowed to stand at room temperature for one hour. The product is obtained by pouring the reaction solution into an excess of water and isolating the precipitate by vacuum filtration. The product yield is 3.6 g. (60%).

EXAMPLE 37

Preparation of O-ethyl S-(1-methylpropyl) N-[2-(5-methylpyridyl)]aminothiocarbonyl phosphoramidothioate To a solution of 1.08 g. (0.01 mole) of 2-amino-5-methyl pyridine in 5 ml. of glyme is added 2.39 g. (0.01 mole) of O-ethyl S-(1-methylpropyl) phosphoroisothiocyanatothioate (exothermic reaction). The solution is allowed to stand at room temperature for two hours and is then poured into an excess of water. The suspension which forms is vacuum filtered and the filter cake is slurried in 50 ml. of hexane. The slurry is vacuum filtered and the filter cake dried to afford 2.2 g. (65%) of product.

EXAMPLE 38

Preparation of N-[2-(5-chloropyridyl)] aminothiocarbonyl O,O-diethyl phosphoramidate To a solution of 2.57 g. (0.02 mole) of 2-amino-5-chloropyridine in 8 ml. of glyme is added 3.9 g. (0.02 mole) of O,O-diethyl phosphoroisothiocyanatoate. The reaction solution is allowed to stand at room temperature for 18 hours. The product is obtained by pouring the reaction solution into an excess of water and isolating the precipitate by vacuum filtration. The product yield is 3.56 g. (55.5%).

EXAMPLE 41

Preparation of O-ethyl S-propyl N-pyrazinyl aminothiocarbonyl phosphoramidothioate To a fine suspension of 0.95 g. (0.01 mole) of aminopyrazine in 5 ml. of acetonitrile is added 2.25 g. (0.01 mole) of O-ethyl S-propyl phosphoroisothiocyanatothioate. The solution which forms is allowed to stand at room temperature for five days and then poured into an excess of water. The suspension is vacuum filtered and the filter cake is washed with ether and dried to afford 0.5 g. (15%) of product.

TABLE I

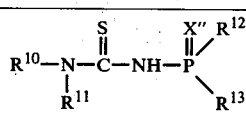

| Ex. No. | X'' | R[10] | R[11] | R[12] | R[13] | M.P., °C. | %C Calc (Found) | %H | %N | %P | %S |
|---|---|---|---|---|---|---|---|---|---|---|---|
| 1 | O | C$_6$H$_5$ | H | OC$_2$H$_5$ | OC$_2$H$_5$ | 109–110 | 45.82 (45.47) | 5.94 (5.90) | 9.72 (9.58) | — | — |
| 2 | S | C$_6$H$_3$Cl$_2$-3,5 | H | OC$_2$H$_5$ | OC$_2$H$_5$ | 89–91 | 35.15 (35.39) | 4.22 (4.05) | 7.30 (7.51) | 8.20 (8.30) | — |
| 3 | O | C$_6$H$_4$CN-4 | H | OC$_2$H$_5$ | OC$_2$H$_5$ | 140–142 | 45.67 (45.99) | 5.12 (5.16) | 13.20 (13.41) | 9.80 (9.88) | 10.15 (10.23) |
| 4 | O | C$_6$H$_4$NO$_2$-4 | H | OC$_2$H$_5$ | OC$_2$H$_5$ | 151–153 | 39.64 (49.84) | 4.84 (47.2) | 12.61 (12.50) | 9.29 (9.03) | — |
| 5 | O | C$_6$H$_3$(CF$_3$)$_2$-3,5 | H | OC$_2$H$_5$ | OC$_2$H$_5$ | 139–140 | 36.80 (37.07) | 3.56 (3.53) | 6.60 (6.53) | — | — |
| 6 | O | C$_6$H$_3$Cl$_2$-3,5 | H | OC$_2$H$_5$ | OC$_2$H$_5$ | 128–130 | 36.99 (37.19) | 4.24 (4.09) | 7.84 (7.81) | — | — |
| 7 | O | C$_6$H$_3$Cl$_2$-3,5 | H | OC$_2$H$_5$ | SCH$_3$ | 138–140 dec. | 33.65 (33.43) | 3.74 (3.65) | 7.73 (7.80) | 8.62 (8.62) | — |
| 8 | O | C$_6$H$_3$Cl$_2$-3,5 | H | OC$_2$H$_5$ | SC$_2$H$_5$ | 133–135 | 35.67 (35.39) | 4.11 (4.05) | 7.58 (7.51) | 8.03 (8.30) | — |
| 9 | O | C$_6$H$_3$Cl$_2$-3,5 | H | OC$_2$H$_5$ | SC$_3$H$_7$n | 122–124 | 37.18 (37.21) | 4.54 (4.43) | 7.33 (7.23) | — | — |
| 10 | O | C$_6$H$_5$ | H | OC$_2$H$_5$ | SC$_3$H$_7$iso | 99–101 | 45.43 (45.26) | 5.98 (6.03) | 8.84 (8.80) | 9.94 (9.73) | 19.67 (20.14) |
| 11 | O | C$_6$H$_3$Cl$_2$-3,5 | H | OC$_2$H$_5$ | SC$_3$H$_7$iso | 138.5– | 37.35 | 4.43 | 7.10 | 7.98 | — |

TABLE I-continued $$R^{10}-\underset{\underset{R^{11}}{|}}{N}-\overset{\overset{S}{\|}}{C}-NH-\overset{\overset{X''}{\|}}{P}\overset{R^{12}}{\underset{R^{13}}{\diagdown}}$$

| Ex. No. | X'' | R¹⁰ | R¹¹ | R¹² | R¹³ | M.P., °C. | %C | %H | %N | %P | %S |
|---|---|---|---|---|---|---|---|---|---|---|---|
| | | | | | | 141 | (37.21) | (4.43) | (7.23) | (8.00) | — |
| 12 | O | C₆H₃(CF₃)₂-3,5 | H | OC₂H₅ | SC₃H₇iso | 127-128 | 37.00 (37.00) | 3.86 (3.78) | 6.00 (6.14) | 6.74 (6.82) | 14.47 (14.11) |
| 13 | O | C₆H₃Cl₂-3,5 | H | OC₂H₅ | SC₄H₉n | 93-96 | 38.61 (38.90) | 4.84 (4.77) | 6.88 (6.98) | — | — |
| 14 | O | C₆H₃Cl₂-3,5 | H | OC₂H₅ | SC₄H₉iso | 108-111 | 38.90 (38.90) | 4.70 (4.77) | 6.84 (6.98) | 7.70 (7.72) | — |
| 15 | O | C₆H₃Cl₂-3,5 | H | OC₂H₅ | SC₄H₉sec | 126-128 | 39.02 (38.90) | 4.87 (4.77) | 7.08 (6.98) | — | — |
| 16 | O | C₆H₄Cl-4 | H | OC₂H₅ | SC₄H₉sec | 83-85 | 42.71 (42.56) | 5.59 (5.50) | 7.43 (7.64) | 8.35 (8.44) | — |
| 17 | O | C₆H₃Cl₂-2,4 | H | OC₂H₅ | SC₄H₉sec | 82-84 | 38.99 (38.90) | 4.81 (4.77) | 6.75 (6.98) | 7.79 (7.72) | — |
| 18 | O | C₆H₃(CF₃)₂-3,5 | H | OC₂H₅ | SC₄H₉sec | 122.5-123.5 | 38.16 (38.46) | 4.15 (4.09) | 5.92 (5.98) | 6.54 (6.61) | — |
| 19 | O | C₆H₄CH₃-4 | H | OC₂H₅ | SC₄H₉sec | 78-80 dec. | 48.42 (48.53) | 6.66 (6.69) | 7.96 (8.09) | 9.12 (8.94) | — |
| 20 | O | C₆H₄OCH₃-4 | H | OC₂H₅ | SC₄H₉sec | 80-83 dec. | 46.00 (46.39) | 6.23 (6.40) | 7.41 (7.73) | 8.46 (8.55) | — |
| 21 | O | C₆H₄N(CH₃)₂-4 | H | OC₂H₅ | SC₄H₉sec | 99-103 dec. | 48.00 (47.98) | 7.15 (6.98) | 11.20 (11.19) | 8.23 (8.25) | — |
| 22 | O | C₆H₃Cl₂-3,5 | H | OC₂H₅ | SC₅H₁₁n | 191.5-194 dec. | 40.34 (40.48) | 4.92 (5.10) | 6.52 (6.75) | 7.42 (7.46) | — |
| 23 | S | C₆H₃Cl₂-3,5 | H | OC₂H₅ | SC₂H₅ | oil | 34.35 (33.93) | 4.18 (3.88) | — | 7.26 (7.96) | — |
| 24 | O | C₆H₃Cl₂-3,5 | H | OCH₂CCl₃ | OCH₂CCl₃ | 142-145 | 23.59 (23.43) | 1.70 (1.61) | 5.06 (4.97) | 5.39 (5.49) | — |
| 25 | O | C₆H₃Cl₂-3,5 | H | N(CH₃)₂ | N(CH₃)₂ | 141.5-144.5 | 37.42 (37.19) | 4.72 (4.83) | 15.73 (15.77) | 8.67 (8.72) | — |
| 26 | O | C₆H₃Cl₂-3,5 | H | OC₂H₅ | N(CH₃)₂ | 143-147 | 37.24 (37.09) | 4.51 (4.53) | 11.96 (11.80) | 8.86 (8.70) | — |
| 27 | O | C₆H₃Cl₂-3,5 | H | OC₂H₅ | C₂H₅ | 107-109 | 38.57 (38.72) | 4.40 (4.44) | 8.20 (8.21) | 8.94 (9.08) | 20.71 (20.78) |
| 28 | O | C₆H₃(CF₃)₂-3,5 | H | OC₂H₅ | C₂H₅ | 98-105 | 38.32 (38.24) | 3.85 (3.71) | 6.42 (6.86) | 7.48 (7.58) | 7.96 (7.85) |
| 29 | O | C₆H₃Cl₂-3,5 | H | SC₃H₇n | SC₃H₇n | 89-91 dec. | 37.21 (37.41) | 4.62 (4.59) | 6.60 (6.71) | 7.42 (7.42) | — |
| 30 | O | C₆H₅CH₂— | H | OC₂H₅ | SC₄H₉sec | oil | 49.52 (48.53) | 6.87 (6.69) | 7.29 (8.02) | 9.03 (8.94) | — |
| 31 | O | C₆H₅CH₂CH₂— | H | OC₂H₅ | SC₄H₉sec | oil | 50.75 (49.96) | 7.15 (6.99) | 7.38 (7.77) | — | — |
| 32 | O | C₆H₁₁cyclo | H | OC₂H₅ | SC₄H₉sec | oil | 46.98 (46.13) | 8.43 (8.04) | 7.46 (8.28) | — | — |
| 33 | O | C₆H₅CH₂ | C₆H₅CH₂ | OC₂H₅ | OC₂H₅ | 103-105 dec. | 58.37 (58.14) | 6.22 (6.42) | 7.06 (7.14) | 7.77 (7.89) | — |
| 34 | O | C₆H₅CH₂ | C₆H₅CH₂ | OC₂H₅ | SC₄H₉sec | 103-106 dec. | 57.77 (57.53) | 6.70 (6.73) | 6.42 (6.67) | 7.10 (7.12) | — |
| 35 | O | 2-pyridyl | H | OC₂H₅ | OC₂H₅ | 137-140 | 41.70 (41.52) | 5.62 (5.58) | 14.58 (14.53) | 10.51 (10.71) | — |
| 36 | O | 3-methyl-6-pyridyl | H | OC₂H₅ | OC₂H₅ | 140-143 | 43.96 (43.56) | 6.12 (5.98) | 13.85 (13.85) | 10.31 (10.21) | — |
| 37 | O | 3-methyl-6-pyridyl | H | OC₂H₅ | SC₄H₉sec | 118-120 | 44.78 (44.94) | 6.08 (6.38) | 12.07 (12.09) | 8.83 (8.92) | — |
| 38 | O | 5-chloro-2-pyridyl | H | OC₂H₅ | OC₂H₅ | 122-125 dec. | 37.31 (37.10) | 4.55 (4.67) | 13.23 (12.98) | 9.36 (9.57) | — |
| 39 | O | fluoren-9-yl | H | OC₂H₅ | OC₂H₅ | 175-176 | 57.56 (57.43) | 5.53 (5.62) | 7.38 (7.44) | 8.30 (8.23) | 8.55 (8.52) |
| 40 | O | fluoren-1-yl | H | OC₂H₅ | OC₂H₅ | 133-135 | 58.33 (57.43) | 5.67 (5.62) | 7.40 (7.44) | 7.72 (8.23) | — |
| 41 | O | pyrazinyl | H | OC₂H₅ | SC₃H₇-n | 106-107 dec. | 37.49 (37.44) | 5.35 (5.37) | 17.49 (17.31) | 9.67 (9.66) | — |
| 42 | O | C₆H₄OH-2 | H | OC₂H₅ | OC₂H₅ | 140-143 | 43.41 (43.16) | 5.63 (5.62) | 9.21 (9.36) | 10.18 (9.85) | — |
| 43 | O | C₆H₄CH₂OH-2 | H | OC₂H₅ | OC₂H₅ | 101-104 | 45.27 | 6.02 | 8.80 | 9.73 | |

TABLE I-continued $$R^{10}-\underset{\underset{R^{11}}{|}}{N}-\overset{\overset{S}{\|}}{C}-NH-\overset{\overset{X''}{\|}}{P}\underset{R^{13}}{\overset{R^{12}}{\diagup}}$$

| Ex. No. | X″ | R¹⁰ | R¹¹ | R¹² | R¹³ | M.P., °C. | ELEMENTAL ANALYSIS Calculated (Found) | | | | |
|---|---|---|---|---|---|---|---|---|---|---|---|
| | | | | | | | %C | %H | %N | %P | %S |
| | | | | | | | (45.38) | (6.10) | (8.98) | (9.69) | |

The present compounds and the metal salts and metal salt complexes thereof (hereinafter collectively referred to as compounds) are active, both therapeutically and prophylactically as anthelmintics. They are especially effective against pinworms and tapeworms.

Initial evaluations of the compounds of this invention are made on the following helminths:

| Common Name | Latin Name |
|---|---|
| Mouse hookworm | Nematospiroides dubius |
| Dwarf tapeworm | Hymenolypis nana |
| Pinworm | Syphacia oblevata |
| Pinworm | Aspiclaris tetraptera |
| Blood Fluke | Schistosomara mansoni |
| Swine roundworm | Ascaris suum |

A preliminary test for anthelmintic activity is carried out by employing animals infected either naturally or experimentally with various helminths. For example, mice are infected with pinworms (*Syphacia oblevata* and *Aspicularis tetraptera*) by exposure to a natural infection of worms one week prior to testing. Mice are infested with tapeworms (*Hymenolypis nana*) by oral intubation of tapeworm egges into the esophagus. After infection, a test diet composed of the test compound(s) homogeneously mixed in ground meal, commercially available under the trademark of Lab-Blox, is placed in feeders where the mice can feed *ad libitum* for a 13 day period. On the tenth, eleventh and twelfth day after the test diet is initiated, the mice are given, by gavage, a mixture of the test compound(s) in ½ percent methylcellulose, once daily for 3 days. On the thirteenth day of the test diet, the test is terminated and the mice necropsied. Efficacy of the test compounds, recorded as percent reduction, is determined from results based on removing and counting the worms.

The compounds of this invention are readily formulated into a variety of suitable pharmaceutical dosage forms such as boluses, tablets, pills, powders, capsules, liquids and suspensions. The dosage forms are prepared using pharmaceutically acceptable carriers and known methods of formulation and manufacture. In the veterinary field, such formulations can be administered in the animals' food.

Representative solid carriers conveniently available and satisfactory for pharmaceutically acceptable, unit dosage formulations include corn starch, powdered lactose, powdered sucrose, talc, stearic acid, magnesium stearate, finely divided bentonite, and the like. The active agent can be mixed with a carrier in varying proportions from, for example, about 0.001 percent by weight in animal food to about 90 or 95 percent or more in a pill or capsule. In the latter form, one might use no more carrier than sufficient to bind the particles of the active compound.

The compounds of this invention should be mixed with animal feeds in a way that will avoid degradation of the compound. Accordingly, administration to animals via their feed will require some information, judgement, and evaluation.

In general, the compounds can be formulated into stable powders or granules for mixing in an amount of feed for a single feeding or enough feed for one day and thus obtain therapeutic efficacy without complication. For prepared and stored feed or feed premixes, a recommended practice is to coat a granular formulation to protect and preserve the active ingredient.

A solid diluent carrier need not be a homogeneous entity, but can be a mixture of different diluent carriers. Moreover, formulations with a solid carrier can include small proportions of adjuvants such as water, alcohols, protein solutions and suspensions, edible oils, sugar solutions, and organic adjuvants such as propylene glycols, sorbitol, glycerol, diethylcarbonate, and the like.

Liquid formulations can also be used. Representative liquid formulations include aqueous (including isotonic saline) suspensions, oil solutions and suspensions, and oil in water emulsions. Aqueous suspensions are obtained by dispersing the active compound in water, preferably including a suitable surface-active dispersing agent such as cationic, anionic, or nonionic surface-active agent.

Representative suitable surface-active agents are polyoxyalkylene derivatives of fatty alcohols and of sorbitan esters, and glycerol and sorbitan esters of fatty acids. Various dispersing or suspending agents can also be included. Representative dispersing or suspending agents are synthetic and natural gums, tragacanth, acacia, alginate, dextran, gelatin, sodium carboxymethylcellulose, methylcellulose, polyvinylpyrrolidone, and the like. The proportion of the active compound in the aqueous suspensions of the invention can vary from about 1 percent to about 20 percent or more.

Oil solutions are prepared by mixing the active compound and an oil, e.g., an edible oil such as cottonseed oil, peanut oil, coconut oil, modified soybean oil, and sesame oil. Usually, solubility in oil will be limited and oil suspensions can be prepared by mixing additional finely divided compound in the oil.

Oil in water emulsions are prepared by mixing and dispersing an oil solution or suspension of the active compound in water preferably aided by surface-active agents and dispersing or suspending agents as indicated above.

In general, the formulations of this invention are administered to animals so as to achieve therapeutic or prophylactic levels of the active compound. The exact concentration of compounds administered can depend upon numerous factors such as the type of animal being treated, its age, weight, and tolerance, the time of administration, and the type and number of helminths present. Thus, dosage rates can vary from about 1 mg. to about 800 mg. per kg. of body weight. A preferred range of dosage rates is from about 5 mg. to about 400 mg. per kg. of body weight. In particular, for use against species of both pinworms and tapeworms, a compound is most desirably administered between about 12 and 100 mg./kg. For use against tapeworms only, the effective dose can be somewhat lower, e.g. about 3 to 50 mg./kg.

The concentration of active compound in the formulation selected for administration is in many situations not critical. One can administer a large quantity of a formulation having a relatively low concentration and achieve the same therapeutic or prophylactic dosage as a relatively small quantity of a relatively more concentrated formulation. More frequent small dosages will likewise give results comparable to one large dose. Unit dosage forms in accordance with this invention can have anywhere from less than 1 mg. to 500 g. of active compound per unit.

If desired, the solid unit dosage forms of this invention including pellets and granules can be coated so as to provide timed release in the digestive system of animals. Such laminated or enteric coated forms are prepared by appropriately applying to a pill or bolus a polymeric acid or a mixture of a polymeric acid with shellac, and cetyl alcohol, cellulose acetate, or styrene maleic acid copolymer.

By way of illustration, Examples I and II present suitable formulations for tablets and chewable tablets, respectively.

EXAMPLE I

A tablet of the following composition is formulated:

| Active Compound | 220 mg. |
| --- | --- |
| Lactose | 53.23 mg. |
| Magnesium Aluminium Silicate Gel | 2.24 mg. |
| Starch | 13.13 mg. |
| Calcium Stearate | 0.65 mg. |
| Microcrystalline Cellulose | 35.75 mg. |
| Total | 325 mg. |

A granulation, containing water by the use of magnesium aluminum silicate and starch in the form of pastes, is tableted to form flat level, double or quarter scored, uncoated tablets of 6 to 9 S.C.A. hardness. The appropriate number (and fraction of tablets) is administered to the host.

EXAMPLE II

An alternate formulation is in the form of a palatable chewable tablet. Each chewable tablet contains:

| Active Compound | 110 mg. |
| --- | --- |
| Dried Fish Meal | 1027 mg. |
| Dried Liver Powder, Bovine | 1027 mg. |
| Soybean Oil Meal | 97 mg. |
| Cane Sugar | 239 mg. |
| Total | 2500 mg. |

The exact concentration of the compound to be employed in the compositions can vary provided that a sufficient amount of the compositions is ingested by the animal so as to provide the required dosage of active agent. The compounds of this invention are useful for killing and controlling parastic worms in ovines, bovines, equines, swine, birds, canines, felines, fish, human beings, and other animals.

The compositions of this invention can be utilized as the sole anthelmintic agent or they can be employed in conjunction with other anthelmintics. Appropriate dosage forms containing a plurality of anthelmintically active compounds are accordingly contemplated by the present invention.

Many variations of this invention are possible without departing from the spirit or scope thereof.

We claim:

1. An anthelmintic composition for oral administration comprising a pharmaceutically acceptable carrier and an anthelmintically effective amount of a compound having the formula:

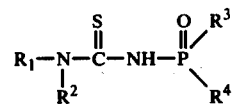

wherein
$R^1$ is (a) a cyclohexyl group,
(b) a benzyl or phenethyl group,
(c) a phenyl group substituted with up to 2 methyl groups, methoxy groups, dimethylamino groups, hydroxymethyl groups, chlorine atoms, trifluoromethyl groups, hydroxyl groups, or cyano groups,
(d) a fluoroenyl group,
$R^2$ is a hydrogen atom or a benzyl group;
$R^3$ is an ethoxy group;
$R^4$ is an ethoxy group, an isobutylthio group, or a sec-butylthio group.

2. A composition according to claim 1 wherein the compound has the formula:

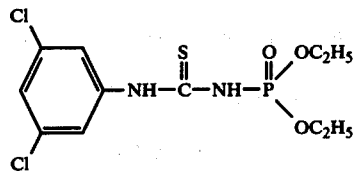

3. A composition according to claim 1 wherein the compound has the formula:

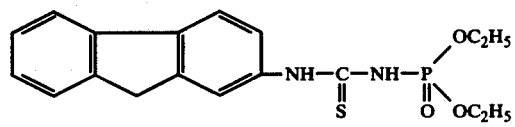

4. A composition according to claim 1 wherein the compound has the formula:

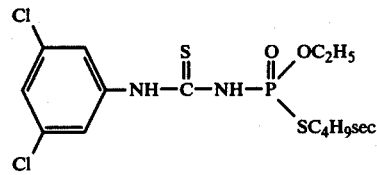

5. A composition according to claim 1 wherein the compound has the formula

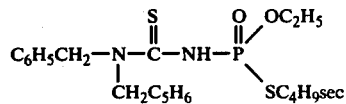

6. A composition according to claim 1, in the form of a tablet.

7. A composition according to claim 1, in the form of a chewable tablet.

8. A composition according to claim 1, in the form of a liquid.

9. A method for controlling a helminth infection in a host animal which comprises orally administering to the animal a composition according to the formula:

$$R^1-N(R^2)-\overset{S}{\underset{\|}{C}}-N(R^3)-\overset{X}{\underset{\|}{P}}(R^4)(R^5)$$

wherein $R^1$ is
- (a) a $(C_3-C_8)$ cycloalkyl group,
- (b) an optionally substituted aralkyl group of up to 11 carbon atoms,
- (c) an optionally substituted $(C_6-C_{14})$ aryl group, $R^2$ is
- (a) a hydrogen atom,
- (b) a $(C_1-C_{10})$ alkyl group,
- (c) a $(C_3-C_8)$ cycloalkyl group,
- (d) a $(C_2-C_{10})$ alkoxyalkyl group,
- (e) a $(C_2-C_{10})$ alkylthioalkyl group,
- (f) a $(C_1-C_6)$ cyanoalkyl group,
- (g) a $(C_3-C_6)$ alkenyl group,
- (h) an optionally substituted aralkyl group of up to 11 carbon atoms, or
- (i) an optionally substituted $(C_6-C_{10})$ aryl group $R^3$ is
- (a) a hydrogen atom,
- (b) a $(C_1-C_{10})$ alkyl group,
- (c) a $(C_3-C_8)$ cycloalkyl group,
- (d) a $(C_3-C_6)$ alkenyl group,
- (e) an optionally substituted aralkyl group of up to 11 carbon atoms, or
- (f) an optionally substituted $(C_6-C_{10})$ aryl group, $R^4$ is
- (a) a $(C_1-C_6)$ alkoxy group,
- (b) a $(C_1-C_6)$ haloalkoxy group,
- (c) a di $(C_1-C_6)$ alkylamino group,
- (d) a $(C_1-C_6)$ alkylthio group,
- (e) a phenoxy group, or
- (f) a phenylthio group, $R^5$ is
- (a) a $(C_1-C_6)$ alkyl group, (b) a $(C_1-C_6)$ alkoxy group,
- (c) a $(C_1-C_6)$ haloalkoxy group,
- (d) a di $(C_1-C_6)$ alkylamino group,
- (e) a $(C_1-C_6)$ alkylthio group,
- (f) a phenyl group,
- (g) a phenoxy group, or
- (h) a phenylthio group; and X is an oxygen or sulfur atom, and the pharmaceutically acceptable metal salts and metal salt complexes thereof.

10. The method of claim 9 wherein the host animal is a mammal.

11. The method of claim 10 wherein the helminths are tapeworms or pinworms.

12. The method of claim 10 wherein the host animal is a swine.

13. The method of claim 10 wherein the host animal is an equine.

14. The method of claim 10 wherein the host animal is a feline.

15. The method of claim 10 wherein the host animal is a canine.

16. The method of claim 10 wherein the host animal is a human being.

* * * * *